United States Patent [19]

Compton et al.

[11] Patent Number: 4,912,031
[45] Date of Patent: Mar. 27, 1990

[54] METHOD FOR DETECTING CARCINOMATOUS AND PRECARCINOMATOUS COLO-RECTAL DISEASE

[75] Inventors: Carolyn C. Compton, Chestnut Hill; Paul J. Durda, Needham, both of Mass.

[73] Assignee: E. I. Du Pont de Nemours and Company, Wilmington, Del.

[21] Appl. No.: 111,667

[22] Filed: Oct. 23, 1987

[51] Int. Cl.$^4$ .................. G01N 33/53; G01N 33/577; A61K 39/00; C12N 1/00
[52] U.S. Cl. .......................................... 435/7; 424/1.1; 424/9; 436/3; 436/548; 436/800; 436/804; 436/813; 530/387; 935/110
[58] Field of Search ................. 435/7, 240, 27, 172.2; 436/503, 548, 813, 800, 804, 536; 935/107, 110; 424/85, 1.1, 7.1, 9; 530/387

[56] References Cited

U.S. PATENT DOCUMENTS

| | | | |
|---|---|---|---|
| 4,579,827 | 4/1986 | Sakamoto et al. | 436/548 |
| 4,678,747 | 7/1987 | Lloyd et al. | 435/7 |
| 4,814,275 | 3/1989 | Durda et al. | 436/513 |

OTHER PUBLICATIONS

Cooper et al., Am. J. Clin Pathol., vol. 69, 1978, p. 594–598.
Talbert et al., Am. J. Clin. Pathol., vol. 88(4), 1987, p. 524.
Compton et al., Cancer, vol. 59, No. 1, Jan. 1987, p. 118–127.
Schoentag et al., Cancer, vol. 53, 1984, p. 503–509.
Allen et al., J. Clin. Pathol. vol. 40, 1987, pp. 157–162.
Erik et al., Archives of Biochemistry and Biophysics, vol. 187, No. 2, Apr. 30, 1978, p. 366–375.
Holmgren et al., British Medical Journal, vol. 288, May 1984, p. 1479–1482.
Kim et al., Cancer Research, vol. 35, Aug. 1975, p. 2092–2097.

*Primary Examiner*—David M. Naff
*Assistant Examiner*—Florina B. Hoffer
*Attorney, Agent, or Firm*—James A. Costello

[57] ABSTRACT

A method for distinguishing between carcinomatous and/or precarcinomatous colo-rectal disease and histologically similar conditions due to diseases that are not carcinomatous or precarcinomatous comprising contacting colo-rectal tissue with an antibody that binds to blood group substance H and determining the presence of carcinomatous or precarcinomatous disease upon a finding of bound antibody, or the absence of such disease upon the finding of no bound antibody.

10 Claims, No Drawings

METHOD FOR DETECTING CARCINOMATOUS AND PRECARCINOMATOUS COLO-RECTAL DISEASE

BACKGROUND OF THE INVENTION

1. Field of the Invention

This invention concerns a diagnostic method for distinguishing between a carcinomatous or precarcinomatous colo-rectal disease and a histologically similar disease which is not carcinomatous or precarcinomatous. This method employs a monoclonal antibody, preferably the antibody IBD-12, which recognizes blood group substance H, an antigen associated with dysplasia in adenomatous colo-rectal polyps.

2. State of the Art

Ulcerative colitis is a chronic, idiopathic inflammatory process of the colon which affects about 0.05% of the population of the Northern industrialized world. The disease is characterized by recurrent bouts of diarrhea and rectal bleeding that may require lifelong medical management. More importantly, it is now well recognized that ulcerative colitis is a premalignant condition, and it has been estimated that about 13% of patients with pancolitis will develop carcinomas. About 1% of all new cases of colon cancer in this country arise as a complication of chronic inflammatory bowel disease. Compared to most colonic malignancies, these cancers tend to occur in a younger age group, to be multifocal, and to behave in a more aggressive fashion.

It is believed that the majority of malignancies in ulcerative colitis can be prevented, because the epithelium of the affected colon undergoes premalignant dysplastic changes prior to the development or carcinoma and these premalignant changes can be detected by regular surveillance biopsies. Since the risk of malignancy increases with duration of disease, being about 5% at 15 years and increasing by 20% with each subsequent decade, yearly colonoscopy and surveillance biopsies are recommended for every patient with ulcerative colitis beginning at 7 to 10 years after diagnosis.

Although seemingly straightforward in theory, the implementation of surveillance has been frought with problems. Six or seven random biopsies from different regions of the colon are usually taken at each colonoscopy. Dysplasia cannot be recognized with the naked eye. Thus, directed biopsy is precluded, and sampling error is a major limitation to the efficacy of the procedure. The biopsy specimens themselves are, in turn, difficult for pathologists to interpret due to the atypical cytologic changes produced by acute inflammation or epithelial regeneration (healing) that resemble dysplasia. Interobserver variation in interpretation of surveillance biopsies varies by 4 to 8% among experienced pathologists and is undoubtedly much higher among nonexpert pathologists. These problems will be greatly alleviated or even eliminated if dysplasia can be recognized both grossly and microscopically.

There are a number of publications concerning ulcerative colitis and carbohydrate expression. However, none of these is directly related to the detection of H substance except Sheahan, Front. gastrointest. Res. Vol. 4, pages 51 to 64 (Karger, Basel 1979). The chemical moiety which defines blood group substance H is an oligosaccharide containing a non-reducing terminal α-L-fucose linked β 1–3 to galactose which in turn is linked β 1¾ to N-acetylglucosamine. The Sheahan article, "Blood Group ABH Isoantigens in Colonic Mucosa of Patients with Inflammatory Bowel Disease", used the lectin, Ulex europaeus, to determine the presence of H substance. Lectins suffer from the drawbacks listed in Compton et al., Cancer 59: 118 to 127 (1987). In particular, Ulex europaeus lectin is inherently less specific than the IBD-12 monoclonal antibody for substance H because the lectin's specificity resides solely in its reactivity with L-fucose residues regardless of what the fucose is attached to, whereas the IBD-12 recognizes the fucose residue only in the context of sugar moieties which are part of blood group substance H.

SUMMARY OF THE INVENTION

This invention concerns a diagnostic method for distinguishing between a condition due to carcinomatous colo-rectal disease and a histologically similar condition that is not carcinomatous, comprising the steps:

(i) contacting the patient's colo-rectal tissue with an antibody-marker conjugate that binds to blood group substance H;

(ii) binding the antibody to colo-rectal tissue that has expressed blood group substance H;

(iii) surveying the tissue for bound antibody; and, (iv) determining the presence of colo-rectal carcinoma in tissue to which antibody is bound and the absence of such disease in tissue to which antibody is not bound.

Any antibody which binds characteristically with blood group substance H is operable in the process of this invention provided it does not also bind to tissue affected by a histologically similar but noncarcinomatous condition. The preferred antibody which meets these criteria is IBD-12, a monoclonal hybridoma antibody specific for the human epithelial antigen, blood group O substance H. The term "monoclonal antibody" as used herein includes the monoclonal antibody solely or a mixture of monoclonal antibodies, monospecific polyclonal (antiserum) antibodies, as well as active fragments derived from any of them. IBD-12 is characterized as follows:

(1) It is secreted by the IBD-12 hybridoma cell line in tissue culture and was shown by conventional immunochemical techniques using appropriate antisera to be an IgMk;

(2) The major immunoglobulin present in the ascites fluid was shown by Ouchterlony analysis to be an IgM;

(3) It is not adsorbed by protein A conjugated to Sepharose when incubated in 0.1M sodium phosphate buffer, pH 8.0;

(4) It has an elution profile from Sepharose 4B consistent with an IgM; furthermore, electrophoretic analysis of the IBD-12 antibody purified on Sepharose 4B indicates that the protein is greater than 90% pure IgM and, upon reduction of the disulfide bonds, the $1 \times 10^6$ Dalton pentameric IgM yields the expected 75,000 Dalton mu heavy chains and 25,000 Dalton light chains assuming an IgM monomer consisting of 2 heavy and 2 light chains having a molecular weight of about 200 KD.

(5) Binding characteristics to various methanol-fixed tumor cell lines as determined in an enzyme-linked immunosorbant assay (ELISA, described in Example) are presented in Table 1:

TABLE 1

| | Cell Line | Absorbance at 488 nm |
|---|---|---|
| Breast | MCF-7 | 1.35 |
| Cell | MDA-MB-231 | 0.45 |
| Lines | HBL-100 | 0.7 |
| | Hs0578T | 0.0 |
| | ZR-75-1 | 0.9 |
| | BT-20 | 1.9 |
| Normal | WI-38 | 0.0 |
| Fibroblast | HEL | 0.0 |
| Cell Lines | | |
| Other | WiDr | 0.55 |
| Tumor | SW-13 | 0.0 |
| Cell | A549 | 0.15 |
| Lines | G-361 | 0.0 |

As Table 1 demonstrates, the IBD12 antibody is reactive with some but not all breast tumor lines, is not reactive with normal fibroblast lines and is reactive with other tumor cell lines including a colo-rectal cell line, WiDr;

(6) The antibody has also been found to be reactive with some lung cancer cell lines such as SHP-77, SW-1573, SkLuci 6 and SkLuci 13, but not with other lung cancer cell lines such as Calu 1, SkMES1, SW-1271 and 9812;

(7) It displays similar reactivities with live unfixed cells from the same cell lines presented in Table 1 indicating that the IBD12 antibody recognizes an antigen which is present on the cell surface.

(8) The reactivities of IBD12 with 6-micron thick sections derived from formalin-fixed, paraffin-embedded patient tissue samples were determined by the immunoperoxidase staining technique described in detail before the Examples.

The method of this invention can be practiced in vivo or ex vivo. The presence of binding can be detected by any procedure that will be obvious to one skilled in the art. For instance, the antibody can be marked or tagged with a stain, an enzyme, a radiolabel, fluorescent label, phosphorescent label and the like to form an antibody-marker conjugate. Enzyme tags employed in the practice of this invention can be used with an enzyme staining protocol to survey for complex formation. Alternatively, an immunological reagent can be used to stain the bound blood group substance H antigen.

One skilled in the art will appreciate that determining the presence or absence of carcinoma according to Step (iv) may rely to some extent on the particular pattern of staining/non-staining (binding/non-binding) that is found. Accordingly, it is contemplated that the Step (iv) determination may rely on interpretation of staining patterns in conjunction with binding/non-binding.

DETAILS OF THE INVENTION

The method of this invention allows the practitioner to distinguish between cellular changes associated with inflammatory diseases which are not life-threatening and carcinomatous changes which are life-threatening or may progress to be life-threatening. The term "carcinomatous" will be used hereafter for the sake of brevity to include both carcinomatous and precarcinomatous conditions. Further characterization of useful antibodies include their recognition of blood group substance H, an antigen associated with dysplasia in adenomatous colo-rectal polyps. The contemplated monoclonal antibody can be used to distinguish between true dysplasia and regenerative/reparative epithelial changes which are not life-threatening. Binding of the antibody is indicative of the presence of H substance and when diffuse epithelial binding is found in the colon it is indicative of a malignant or premalignant lesion. Often in early stage ulcerative colitis there are cellular changes which mimic such neoplastic changes. Use of the disclosed antibodies by the method of this invention will distinguish such benign regenerative changes from malignant/premalignant changes.

Useful antibodies, including IBD-12, can be produced by the following procedure known generally in the art: (a) immunize mice with a certain immunogen; (b) remove the spleens from the immunized mice and make a spleen suspension in an appropriate medium; (c) fuse the suspended spleen cells with mouse myeloma cells from a suitable cell line; (d) dilute and culture in separate containers the mixture of unfused spleen cells, unfused myeloma cells and fused cells in a selective medium which will not support the unfused myeloma cells, for a time sufficient to allow death of all the unfused cells; (e) evaluate the supernatant in each container containing a hybridoma for the presence of antibody to the immunogen; and (f) select and clone hybridomas producing the desired antibodies. Once the desired hybridoma has been selected and cloned, the resultant antibody is produced by in vitro culturing of the desired hybridoma in a suitable medium. In an alternative method, the desired hybridoma can be injected directly into mice intraperitoneally to produce an ascites fluid.

The cell line secreting IBD-12 has ATCC Accession No. HB8751. A more detailed procedure for making IBD-12 is as follows.

PROCEDURE FOR MAKING IBD-12

The general method used for production of antibody-secreting somatic cell hybrids was described by Gefter et al. in Somatic Cell Genetics 3, 321 (1977) and by Marshak-Rothstein et al. in Jour. Immuno. 122, 2491 (1979). Briefly, a Balb/c mouse was immunized intraperitoneally on day zero with MCF-7 (ATCC Accession No. HTB22) membranes (100 μg of protein) mixed 1:1 with complete Freunds adjuvant 0.2 mL total volume. The mouse was boosted on days 51 and 73 with the same amount of immunogen mixed 1:1 with incomplete Freunds adjuvant. On day 100, the mouse was boosted with 100 μg of immunogen mixed 1:1 with complete Freunds adjuvant.

Four days layer, the spleen of the mouse was removed and fused with the non-secretor myeloma cells of cell line P3 x Ag8, varient 653, ATCC Accession No. CRL 1580; see Kearney et al. Jour. Immunol. 123, 1548 to 1550 (1979). More particularly, after sacrifice of the mouse, a spleen cell suspension was prepared in RPMI 1640 medium ($5 \times 10^7$ lymphocytes/ml). To 1 ml of spleen cells was added $5 \times 10^6$ myeloma cells, P3 x Ag8, varient 653 in a round bottom plastic tube. This cell mixture was centrifuged at 700 xg for five minutes at room temperaure. After removal of the supernatant, the cells were suspended by tapping the tube and 0.5 ml of 37° C., 30% w/v polyethylene glycol 1000 (PEG) (Baker Chem. Co.) was added. The cells with PEG were immediately centrifuged at room temperature 700 xg for 3.5 minutes. Ten minutes after the addition of PEG, the cells were gently resuspended and 4.0 ml of RPMI 1640 was added to the tube. This suspension was then poured into a 100 mm diameter Petri dish containing 4.5 ml of RPMI 1640 and 1.5 ml of horse serum. These cells were then incubated at 37° C. for 18 to 24 hours. The cells were then gently resuspended and diluted to 65 ml in RPMI 1640 containing 10% horse serum and hypoxanthine/aminopterin/thymidine (HAT; $10^{-6}M:8\times10^{-10}M:1.6\times10^{-7}M$, respectively).

Cells were then pipetted at two drops/well into 96 well microtiter plates (approximately $2\times10^5$ spleen cells/well). Approximately 14 days later, tissue culture supernates from wells containing colonies were tested for binding to MCF-7 cells by the following procedures. Procedure (1): An enzyme-linked immunosorbant assay (ELISA) procedure wherein MCF-7 cells were grown in 96 well polyvinyl chloride microtiter plates (CoStar Cat. No. 2596) until approximately confluent. The microtiter plates had been coated with 0.1% w/v poly-L-lysine (Sigma P-0879), m.w. 4000, and subjected to u.v. sterilization prior to being used for growing cells. These adherent cells were fixed by dipping the plate in 100% methanol followed by air drying. Hybridoma supernates were added to the wells containing fixed MCF-7 cells, and plates were incubated at 4° C. for 16 to 20 hours. Hybridoma supernates were then removed by aspiration and the wells were washed three times with PBS buffer containing 1% w/v serum albumin (PBSBSA).

Then, 100 μl of PBSBSA diluted anti-mouse IgG antibody conjugated to horse radish peroxidase (GAMHRP) (New England Nuclear Corp.) diluted 1:500 in PBSBSA was added to the wells, followed by incubation at 37° C. for one hour. GAMHRP was then removed by aspiration and the wells washed once with 100 μl of PBSBSA and twice with distilled water. Presence of bound GAMHRP was determined by adding to the wells 100 μl of the substrate of HRP, 0.2% w/v o-phenylenediamine in citrate-phosphate buffer (0.009M citric acid, 0.03M $K_2HPO_4$) containing 0.015% hydrogen peroxide. HRP in combination with its substrate resulted in a yellow colored product; development of the product was allowed to occur at room temperature for 10 to 20 minutes. The enzymatic reaction was terminated by the addition of 100 μl of 4.5M $H_2SO_4$. Measurement of the resultant reaction product was accomplished by determining optical density at 488 nm. Presence of yellow color in the wells indicated that antibody was present in the hybridoma supernatants which could bind to fixed MCF-7 cells and be recognized by the GAMHRP reagent. Procedure (2): Hybridoma supernates were added to the wells of microtiter plates made of soft plastic. The microtiter plates had been coated with BSA prior to use. Then, 100 μL of 20 mM tris maleate pH 6.8 and 10 μL of MCF-7 membranes (approximately 7 μg of protein/mL) were added to each well. The hybridoma supernates were incubated with the MCF-7 membranes for 1 to 1½ hours at 30° C. or overnight at 4° C. Then, either 10 μL of a mixture of 5 mM $MnCl_2$ and CMP($^3H$)NANA (NEN Corp.) and 10 μL of desialylated, degalactosylated fetuin (25 mg protein/mL) or 10 μL of a mixture of 5 mM $MnCl_2$ and UDP($^3H$)Gal (NEN Corp.) and 10 μL of desialylated, degalactosylated fetuin (25 mg protein/mL) was added to each well. Control plates containing tritiated nucleotide sugars, but not the fetuin, were also set up. Plates were incubated for 2 to 2½ hours at 37° C. Ice cold TCA was then added to each well. The plates were stored at 4° C. for 10 minutes, then centrifuged for 10 minutes. After aspiration, the microtiter wells were cut out of the plates and the $^3H$-sugars were counted by conventional liquid scintillation counting procedures.

Cells in wells containing hybrids secreting an IgG that bound to MCF-7 cells as determined by Procedure (1), that inhibited the transfer of a sugar from a nucleotide-sugar to a carbohydrate moiety associated with MCF-7 membranes as determined by Procedure (2), and that did not inhibit the activity of a glycosyltransferase enzyme associated with the MCF-7 membranes as determined by Procedure (2) were expanded and subjected to limiting dilution cloning.

After limiting dilution cloning, ascites fluid containing the MCF-7 reactive antibody was produced in Balb/c mice as follows. Mice were primed with 0.5 mls of Pristane ® (Aldrich Chem. Co.) by intraperitoneal (i.p.) injection two weeks prior to i.p. innoculation with $1\times10^6$ cloned IBD12 hybridoma cells. After two to three weeks, the ascites fluid was removed with a syringe. Presence of MCF-7 reactive antibody was determined using Procedure (1) described above with various dilutions of the ascites fluid. Those samples showing the highest titer (1:10,000 to 1:50,000) were pooled and subjected to salting out with 50% ammonium sulfate at 4° C. Precipitate containing the IBD12 antibody was collected by centrifugation and dissolved in distilled water. This material was then subjected to gel filtration chromatography on Sepharose 4B ® (Pharmacia) and the peak containing reactivity for MCF-7 cells pooled to provide partially purified IBD12 antibody.

EXAMPLES 1 TO 7

To determine the reactivity of IBD-12 with various tissues, ex vivo, formalin-fixed paraffin-embedded tissue sections were employed. Immunoperoxidase staining techniques were carried out according to the following protocol:

(A) 10% formalin-fixed, paraffin-embedded, 6 micron sections from colo-rectal tissue samples are cut on a table top microtome. Sections are picked up on albumin coated slides and baked at 56° C. for two to three hours.

(B) The sections are deparaffinized in 100% xylene for 30 minutes, then in 100% ethanol for 5 minutes. Endogenous peroxide is quenched by a 30 minute incubation with 0.6% hydrogen peroxide in 100% methanol.

(C) The sections are rinsed in PBS and blocked with 10% normal goat serum in PBS containing 1% BSA (PBS:BSA).

(D) The slides are wiped dry and 200 to 500 μg/ml in PBS:BSA are added over the tissue section. The sections are then incubated in a humidified chamber for 90 to 120 minutes at room temperature. Each tissue section sample is tested with a class-matched, IgM, and normal saline controls are run.

(E) The tissue sections are washed extensively in PBS. This washing is carried out in separate staining trays to ensure that specific Ab samples are kept separate from the control slides.

(F) A secondary antiserum consisting of rabbit anti-mouse IgM (Miles Labs) is added to all tissue sections at a dilution of 1:100 in PBS:BSA. This is then incubated at room temperature in the humidified chamber for 30 minutes.

(G) The sections are washed three times with PBS and subsequently incubated with goat anti-rabbit IgG:biotin at a dilution of 1:200 in PBS:BSA. The goat anti-rabbit IgG:biotin is part of an ABC Immunoperoxidase kit from Vector Laboratories.

(H) The sections are washed three times with PBS and incubated with the avidin-biotin-horseradish peroxidase complex (part of the above ABC kit) diluted 1:100 in PBS:BSA. Incubation is at room temperature for 30 minutes.

(I) Following five washings with PBS, diaminobenzidine at a concentration of 400 µg/ml in PBS is added to the sections.

(J) After incubation for approximately 10 minutes, the sections are washed once with PBS and twice with distilled water. They are then counterstained in double strength Gill's hematoxylin (Lerner Labs) for two minutes; washed in water; dipped in 0.03M acetic acid; washed in water again; developed in 0.01% ammonium hydroxide; washed in water; and finally dehydrated through 95% ethanol, 100% ethanol, and 100% xylene. Sections are then treated with Permount ® and coverslips are placed over the sections. The resulting slides were then examined visually.

Employing the IBD-12 antibody at 4 to 10 µg/tissue section yielded strong staining of tumor cells in samples from patients with colon carcinoma. A reddish-brown color was detected and was attributed to the presence of the reaction product of horseradish peroxidase which in turn is bound through various intermediates to IBD-12. Hematoxylin, which yields blue staining of nuclei, was used as a counterstain to heighten the contrast with reddish-brown precipitates. The material staining with the antibody appears to be secreted, attached to the cell surface, and cytoplasmic.

The following results were obtained using total colectomy specimens from patients with long-standing ulcerative colitis:

(1) Positive, though sometimes discontinuous, staining of all cancers regardless of stage, grade, or histologic type.

(2) Positive staining of all high grade dysplasia in a diffuse, though sometimes discontinuous, pattern.

(3) Positive staining of some low grade dysplasia, also in a diffuse pattern.

(4) No staining of chronic quiescent colitis without dysplasia.

(5) No staining of acutely inflamed epithelium.

(6) No staining of uninvolved mucosa (regions of colon spared of inflammatory bowel disease).

(7) Focal staining of single cells or small numbers of adjacent cells at the bases of regenerating glands or at the edges of reepethelializing ulcers in post-ulceration recovery/repair.

Staining patterns described in summaries 1 through 7 were interpreted by a practitioner of pathology as indicative of carcinomatous conditions in 1, 2 and 3 and non-carcinomatous conditions in 4 through 7.

EXAMPLE 8

An in vivo application of the method of this invention to distinguish between a carcinomatous vs. a noncarcinomatous condition could be as follows. Fluorescent or phosphorescent tagged antibody can be introduced into the evacuated colon in an appropriate physiological buffer. After sufficient incubation time to allow binding of the antibody to tissues expressing H substance, the unbound antibody can be washed out by enema with a physiological buffer such as PBS. Binding of the tagged antibody to the colonic or anal/rectal epithelium can be determined by fluorescent or visible light colonoscopy, employing a light source to excite the fluorescent or phosphorescent tag attached to the antibody to determine if the antibody is present. If tagged antibody is present, it would result in a light signal that the medical practitioner could monitor. Any tissues found to bind tagged antibody could then be biopsied and tested ex vivo, by a procedure such as that described with respect to Examples 1 to 7, to confirm the inappropriate presence of H substance. Such directed biopsies would increase the chances of evaluating relevant tissue samples as opposed to the present procedure of evaluating random tissue biopsies.

The embodiments of the invention in which an exclusive property or privilege is claimed are defined as follows:

1. A method for distinguishing, in a patient's colo-rectal tissue, between a colo-rectal carcinoma and histologically similar inflammatory, regenerative or reparative changes that are not carcinomatous, comprising the steps:
    (i) contacting the patient's colo-rectal tissue with a conjugate of IBD-12 antibody and a marker selected from the group consisting of a stain, an enzyme, a radiolabel, a fluorescent label, and a phosphorescent label,
    (ii) surveying the tissue for any bound conjugate of IBD-12 and marker, and
    (iii) determining the presence of colo-rectal carcinoma in tissue to which IBD-12 is bound in a diffuse pattern and the absence of such disease in tissue to which IBD-12 is not bound or is bound in a focal pattern; wherein the IBD-12 is secreted by cell line bearing ATCC Accession No. HB8751.

2. A method according to claim 1 conducted in vivo.

3. A method according to claim 1 conducted ex vivo.

4. A method according to claim 1 wherein the marker is a stain.

5. A method according to claim 1 wherein the marker is an enzyme.

6. A method according to claim 1 wherein the marker is a radiolabel.

7. A method according to claim 1 wherein the marker is a fluorescent label.

8. A method according to claim 1 wherein the marker is a phosphorescent label.

9. A method according to claim 1 employing an immunological reagent to stain bound blood group substance H.

10. A method according to any one of claims 2 and 4 to 9 comprising determining the presence of bound conjugate by colonoscopy.

* * * * *